United States Patent
Gusi (10) Patent No.: US 7,965,099 B2
(45) Date of Patent: Jun. 21, 2011

(54) BUS MODEM FOR BUILDING AND INDUSTRIAL ELECTRICAL SYSTEMS

(75) Inventor: Piero Camillo Gusi, Marostica (IT)

(73) Assignee: Vimar S.p.A., Marostica Vicenza (IT)

( * ) Notice: Subject to any disclaimer, the term of this patent is extended or adjusted under 35 U.S.C. 154(b) by 451 days.

(21) Appl. No.: 11/915,826

(22) PCT Filed: Jun. 6, 2006

(86) PCT No.: PCT/EP2006/005448
§ 371 (c)(1),
(2), (4) Date: Sep. 22, 2008

(87) PCT Pub. No.: WO2007/003254
PCT Pub. Date: Jan. 11, 2007

(65) Prior Publication Data
US 2009/0016419 A1    Jan. 15, 2009

(30) Foreign Application Priority Data
Jul. 1, 2005 (IT) .............................. MI2005A1248

(51) Int. Cl.
*H03K 17/16* (2006.01)
*H03K 19/003* (2006.01)
*H03K 3/00* (2006.01)

(52) U.S. Cl. ........................................ 326/30; 327/111

(58) Field of Classification Search .................... 326/68, 326/80–83, 86, 87
See application file for complete search history.

(56) References Cited

U.S. PATENT DOCUMENTS

| 5,572,158 | A  | * | 11/1996 | Lee et al. ....................... 327/175 |
| 5,932,976 | A  | * | 8/1999 | Maheshwari et al. ........ 315/291 |
| 6,853,562 | B2 | * | 2/2005 | Zhang ......................... 363/21.06 |
| 7,692,391 | B2 | * | 4/2010 | Nakada et al. ................. 315/291 |
| 2004/0257119 | A1 | * | 12/2004 | Watanabe et al. ................ 327/54 |
| 2005/0152158 | A1 | * | 7/2005 | Gut et al. ......................... 363/16 |
| 2005/0220938 | A1 | * | 10/2005 | Abe et al. ......................... 426/56 |

FOREIGN PATENT DOCUMENTS

| EP | 0854587 A1 | 7/1998 |
| JP | 04/200022 A | 7/1992 |
| WO | WO 93/08652 A | 4/1993 |
| WO | WO 96/02982 A | 2/1996 |

* cited by examiner

*Primary Examiner* — Vibol Tan
*Assistant Examiner* — Dylan White
(74) *Attorney, Agent, or Firm* — Banner & Witcoff, Ltd.

(57) ABSTRACT

A bus modem for building and industrial electrical systems comprises a module (100) which comprises a pair of input pins (1, 2) destined to be connected to the bus and a pair of output pins (9, 10) destined to be connected to the electrical circuit of a device to be connected to the bus. The module (100) further comprises a voltage control circuit (3) able to take voltage from said bus and to control the voltage ($V_{ASB}$) on a capacitor (C1) disposed at the terminals of said output pins (9, 10), and a transmission control circuit (5) able to control an electronic switch (7) which controls a current limiting circuit (8) able to limit the current on the bus, during transmission of signals from the bus to the devices connected to the bus and vice versa.

16 Claims, 7 Drawing Sheets

Fig. 1

PRIOR ART

Fig. 2

PRIOR ART

BUS MODEM FOR BUILDING AND INDUSTRIAL ELECTRICAL SYSTEMS

This application is a national stage application of co-pending PCT application PCT/EP2006/005448 filed Jun. 6, 2006, which claims priority of Italian Application No. MI2005A001248, filed Jul. 1, 2005. The disclosure is expressly incorporated herein by reference.

BACKGROUND

The present invention refers to a modem device for bus communication for building and industrial electrical systems, such as for example the bus known by the commercial name of "Konnex TP1 bus", which makes it possible in a residential, tertiary and industrial setting to achieve integrated management of various systems such as, for example, electrical, heating, air conditioning, irrigation and anti-intrusion systems and technical alarms, such gas, water and smoke detectors.

SUMMARY

The modem according to the invention allows the supply voltage necessary for operation of the various control devices to be taken from the bus and provides the possibility of decoding the signals transmitted on the bus and of coding the signals to be transmitted on the bus.

Communication between the modem and the bus is of the half-duplex, two-way type and the transmission support of the exchanged data is achieved by means of a single twisted pair of wires, also known as a duplex cable.

The voltages present on the bus conductor cable are of the SELV (Safety Extra Low Voltage) type.

In this application field, integrated devices produced by Siemens are present on the market with the function of modems for the Konnex TP1 bus. Examples of such modem devices are described in European patent EP 0 770 285.

Two components are known to the art: FZE 1066-EIB Twisted Pair Transceiver and EIB-TP-UART-IC.

The first component is an integrated modem which mainly allows an interface to be created between the bus and a microcontroller. In fact it makes it possible to generate from the bus various supply voltages, interface signals for the microcontroller, decoding of the signal on the bus and coding of the messages to be transmitted.

The messages transmitted on the bus are superimposed on the direct supply voltage ranging between about 20 V and 30 V. This is a digital signal where the single bit "0" is obtained by achieving a voltage drop of about 7V with a duration of about 35 µs. The bit lasts 104 µs in all, resulting in a transmission at 9600 baud. The bit "1" on the other hand does not lead to significant variations in the direct voltage of the bus.

Figure 1:
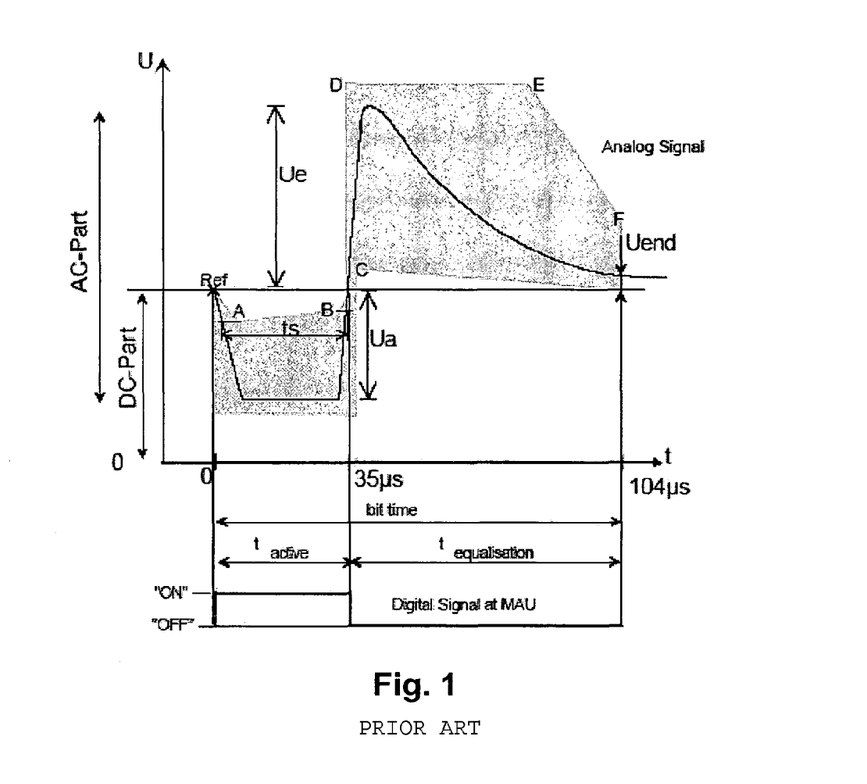
FIG. 1 is a diagram illustrating the specifications for transmission of the bit "0" in the Konnex TP1 bus.
Figure 2:
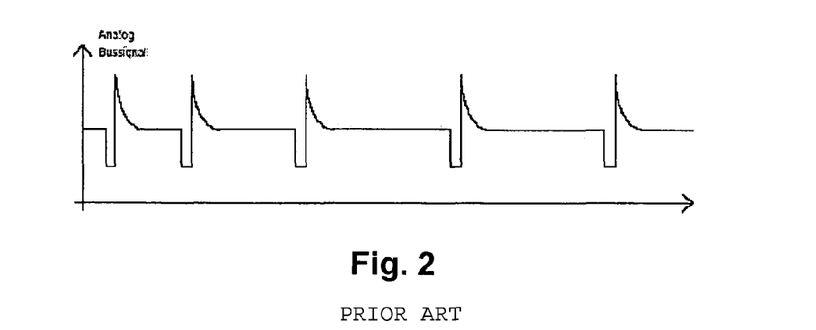
FIG. 2 is a diagram illustrating a generic sequence of bits transmitted on a bus.

In FIG. 1 the specifications of the Konnex bus for transmission of the bit "0" are shown by way of example. In FIG. 2, on the other hand, a diagram is shown illustrating bus transmission of a sequence of bits.

The main function of the FZE 1066 modem is to obtain the various supplies of the devices, in such a manner as to disturb the signal transmission on the bus only minimally. In particular such a modem must not load the rising and falling edges in the creation of the voltage drop and must cause only a minimal variation of the current on the bus when messages are being transmitted.

As far as decoding of the messages present on the bus is concerned, the modem decodes each individual bit, adapting the levels of the signals present on the bus to those necessary for a microcontroller. All edges of transmitted bits are decoded without any analogical or digital filtering action.

The third basic characteristic of the FZE 1066 modem is that of converting the messages transmitted by the microcontroller into voltage levels suitable to be transmitted on the bus. This must be able to generate voltage drops on the bus with adequate depth and edges.

As far as the second modem device EIB-TP-UART-IC is concerned, the essential difference with respect to the first one lies in the decoding of the bytes of messages present on the bus, that is, it converts the TP type messages present on the bus into UART to be sent to a microcontroller and vice versa.

Object of the present invention is to realize a modem circuit for bus communication, in particular for a Konnex TP1 bus, which is extremely versatile, easily adaptable to various applications for controlling, through the bus, various types of devices.

Another object of the present invention is to provide such a bus modem that is modular, composed of various flexible modules that can be added to the bus according to the needs of the various devices that are to be connected to the bus.

Yet another object of the present invention is to provide such a bus modem wherein the modules provide interchangeable components which can be added according to the various needs.

Yet another object of the present invention is to provide such a bus modem that has a limited number of discrete components, so as to optimize costs and space occupied.

These objects are achieved in accordance with the invention with the characteristics listed in appended independent claim 1.

Advantageous embodiments of the invention are apparent from the dependent claims.

The bus modem for building and industrial electrical systems according to the invention comprises a module which comprises a pair of input pins designed to be connected to the bus and a pair of output pins designed to be connected to the electrical circuit of a device to be connected to the bus. The module further comprises:

a voltage control circuit able to take the voltage from the bus and to control the voltage on a capacitor disposed at the terminals of the output pins, and
a transmission control circuit able to control an electronic switch which controls a current limiting circuit able to limit the current on the bus during transmission of signals from the bus to the devices connected to the bus and vice versa.

The main advantage of this type of system is flexibility, understood as the possibility of being able to program and re-program functions and controls at will.

Connection between the devices takes place in a "logical" manner. Each component, even those performing the simplest functions such as for example a pushbutton, is able to receive and to transmit encoded signals and commands on the bus cable. The data thus transmitted circulates on the bus and is received only by the apparatus for which it is intended.

The individual control, signalling and actuating devices can be connected at any point of the bus, without any particular logic. Functions and logical connections are defined by means of an adequate configuration procedure.

The correlations and operating conditions of the system are modified by modifying the system configuration without intervening on the wiring. This is a fundamental opportunity not only in the residential setting but also in the tertiary and industrial setting, where the need to modify the designated use or the division of operating environments (offices, opens spaces, mobile partitions) is more frequent.

The versatility of the system therefore becomes complete. At any time the use of the components can be "re-programmed" to better meet the needs for use of each room.

Any client request can be fulfilled, offering each a personalized, dedicated solution able to meet specific needs.

Installation is also far easier than for a traditional system. No dedicated wiring is needed for the control devices; a simple twisted duplex cable is sufficient to connect to each other all the domotic devices of the system. Communication between the various devices takes place in the form of digital packets. Each packet contains a certain number of bytes, generally not more than ten. The packets are often called with equivalent terms: messages, telegrams or frames. Typical transmission speeds are 9.6 kbit/s.

Sharing of the communication means makes it possible for only one element at a time to access the bus to transmit data; otherwise, in the event of simultaneous access, collisions occur. The maximum number of devices that can be connected depends upon many factors and generally does not exceed 256.

However, using devices known as "couplers" it is possible to connect more than 10,000 devices. The maximum length of the bus cable is limited by signal attenuation. Without making use of "couplers" distances of the order of a kilometer can be reached, more than enough for the majority of systems.

Connections between the devices can be made in the following ways:
  linear: there is a single backbone to which all the devices are connected;
  star: each individual device is connected to a central point;
  tree: branches that connect a plurality of devices depart from a central backbone;
  free: this is the combination of all the modalities described above.

DESCRIPTION OF THE DRAWINGS

The characteristics and the advantages of the invention will be made clearer by the detailed description of embodiments made below by way of non-limiting example, with reference to the appended figures, in which.

DETAILED DESCRIPTION

The bus modem according to the invention is described with the aid of the figures.

Figure 3:
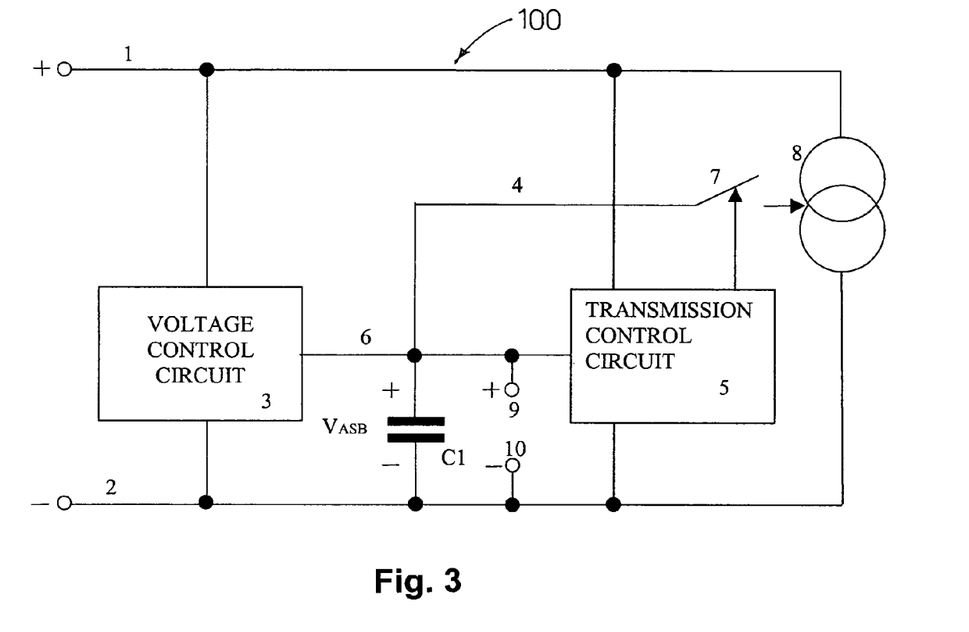
FIG. 3 is layout block diagram illustrating a first module of the bus modem according to the invention.
Figure 4:
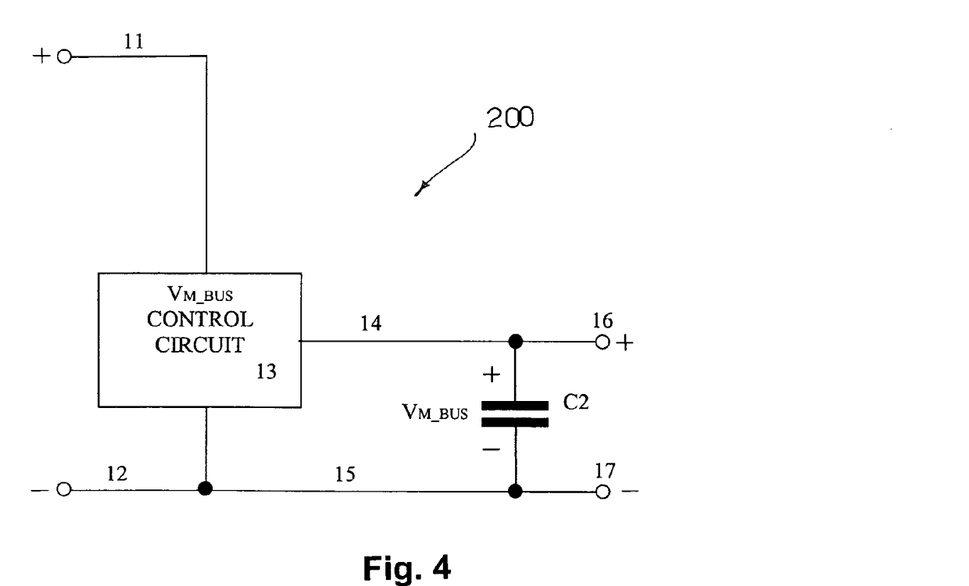
FIG. 4 is a layout block diagram illustrating a second module of the bus modem according to the invention.

The modem according to the invention comprises a first module 100 whose layout is illustrated in FIG. 3 and a second optional module 200 whose layout is illustrated in FIG. 4.

As shown in FIG. 3, the first module 100 of the modem comprises two input pins 1 and 2 destined to be connected to the bus and two output pins 9 and 10 destined to be connected to the circuit of a device connected to the bus, such as for example a domotic device.

Between the pins 1 and 2 is disposed a $V_{ASB}$ control circuit denoted by 3, able to control the voltage $V_{ASB}$ at the terminals of the output pins 9 and 10. The $V_{ASB}$ control circuit is connected, by means of a connection 6, to a capacitor C1 disposed between the output pins 9 and 10. Thus the $V_{ASB}$ control circuit keeps the capacitor C1 charged to control the voltage at the terminals of the pins 9 and 10.

The module 100 comprises a transmission control circuit 5, which controls a current limiting circuit 8, acting on a switch 7. The switch 7 is connected by means of a connection 4 to the output pin 6 of the $V_{ASB}$ control circuit 3 and to the current limiting circuit 8. The transmission control circuit 5 is disposed between the input pins 1 and 2 and is connected to the output pin 9 and to the switch 7.

The $V_{ASB}$ control circuit 3 must supply the capacitor C1 from which the majority of the various electronic control circuits of a domotic device destined to be connected to the bus take their supply. Object of the $V_{ASB}$ control circuit 3 is to take the necessary current from the bus without interfering with the messages transmitted on the bus. Absorption of current must not vary appreciably when voltage drops occur due to the bits transmitted on the bus.

The capacitor C1 serves as a low-pass filter and therefore, if the $V_{ASB}$ control circuit 3 is correctly sized, the maximum adjustment frequency is lower than the minimum transmission frequency. This ensures that the resistance of the $V_{ASB}$ control circuit 3 is sufficiently low for the supply of the circuits connected between the pins 9 and 10 and sufficiently great for the signals transmitted on the bus.

In practice it is useful to set the maximum adjustment frequency one-tenth lower than the minimum transmission frequency.

Figure 5:
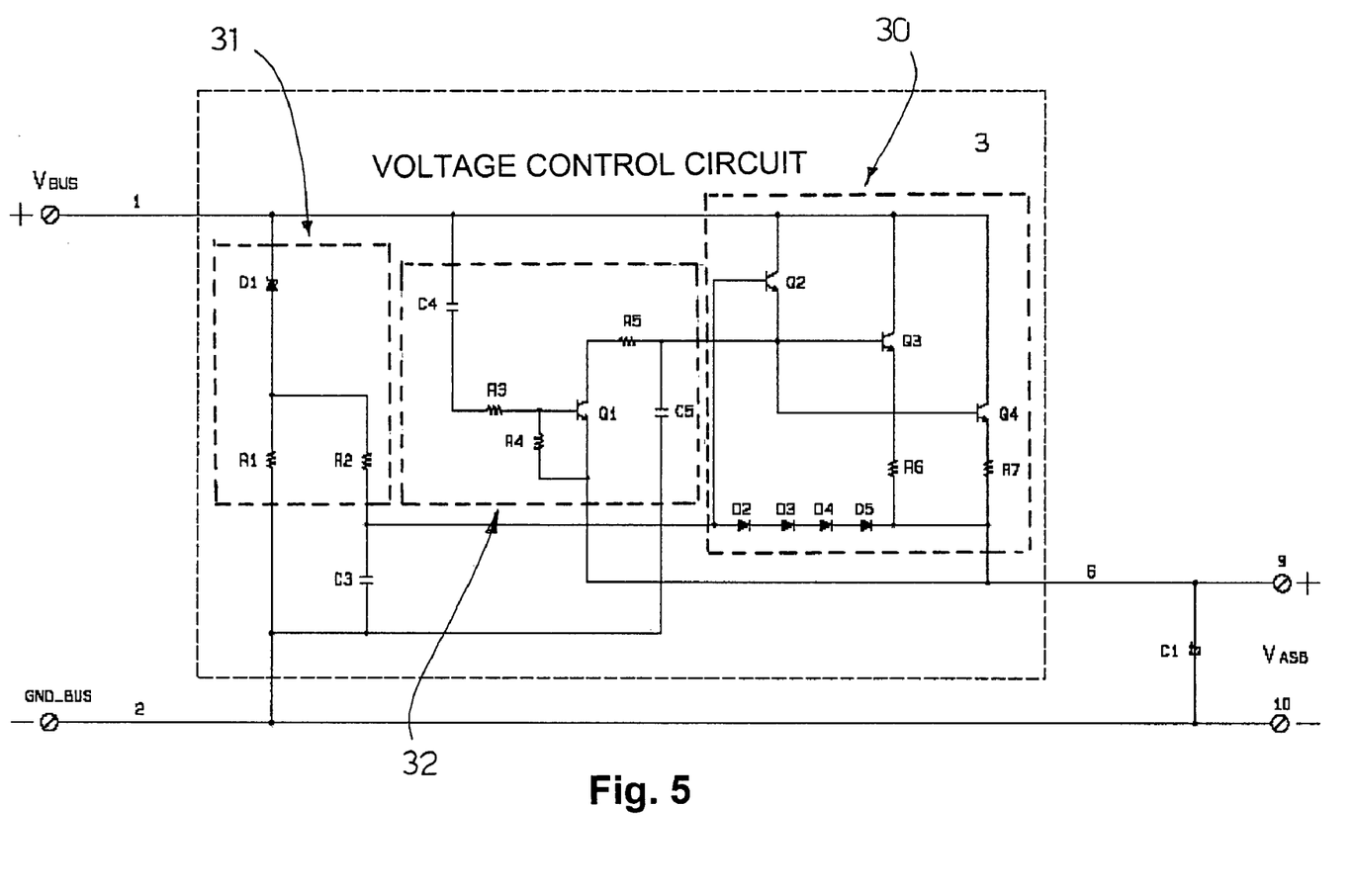
FIG. 5 is a circuit diagram illustrating in detail an embodiment of the control circuit $V_{ABS}$ of the first module of FIG. 3.

In FIG. 5, by way of example, a possible embodiment of the $V_{ASB}$ control circuit 3 of FIG. 3 is illustrated.

The $V_{ASB}$ control circuit 3 comprises a capacitor C3 charged by a charging circuit 31 comprising a Zener diode D1 in series to a resistor R1 disposed between the input pins 1 and 2. A resistor R2 has a terminal connected between D1 and R1 and the other terminal connected to the capacitor C3.

The stabilized voltage of C3 is used to control the voltage on C1, by means of a voltage stabilizer circuit 30 comprising three transistors Q2, Q3 e Q4. The collectors of Q2, Q3 and Q4 are connected to the pin 1 and the emitter of Q2 is connected to the bases of Q3 and Q4. Between the base of Q2 and the emitter of Q3 there are disposed four diodes in series D2, D3, D4 e D5. Furthermore the base of Q2 is connected between the resistor R2 and the capacitor C3 and a resistor R6 is connected to the emitter Q3. A resistor R7 is connected between the emitter of Q4 and the output pin 6 of the $V_{ASB}$ control circuit.

The $V_{ASB}$ control circuit 3 comprises a power consumption reducing circuit 32 able to reduce power consumption of the $V_{ASB}$ control circuit 3.

The power consumption reduction circuit 32 comprises a capacitor C4 connected to the pin 1 in series to a resistor R3 and to a resistor R4 disposed between the base and the emitter of a transistor Q1. The collector of Q1 is connected by means of a resistor R5 and of a capacitor C5 to the pin 2.

By means of the Zener diode D1 and of the resistors R1 and R2, the capacitor C3 is charged at a voltage about 10 volts lower than the mean voltage present on the bus.

The charge constant R2×C3 is such as to ensure a voltage without ripples on the capacitor C3, even when transmission frames are present on the bus.

Furthermore, given that the bus, because of the resistance of the conductor cable and of the various distributed devices, has a voltage that decreases as the distance from the power supply increases, the capacitor C3 has a stabilized voltage reduced by the value of the Zener diode D1, variable in the range allowed by the bus voltage.

The stabilization value proves lower than the minimum bus voltage value when frames are being transmitted. The voltage of the capacitor C3 is used as the reference voltage to realize a voltage stabilizer, by means of the transistors Q2, Q3 e Q4.

The transistor Q2 serves as a current amplifier for Q3 and Q4. The diodes D2, D3, D4, D5 together with the resistors R6 e R7 and the transistors Q2, Q3 and Q4 perform the function of maximum current limiters both when the device is switched on and in the event of an excessive absorption by the control circuit 3 on $V_{ASB}$ between the pins 9 and 10. The transistor Q4 and the resistor R7 can be omitted, if power consumption of the circuit downstream so allows.

The capacitor C4 acts on the base of the transistor Q1 and activates it for a brief period coinciding with the positive edges of the bits transmitted on the bus. This makes it possible to discharge the capacitor C5 to a minimal extent so as to reduce the power consumption of the device for a short period.

This favours the overvoltage on the bus generated by the bit "0" transmitted. This specification is formalized in the Konnex specifications, Volume 8 System Conformance Testing, chapter 5 Receiver, paragraph 5.1 Pulse-Impedance.

The capacitor C1, like the capacitor C3, has a stabilized tension lower than the minimum value of the tension present on the bus when frames are being transmitted. This ensures that the current absorbed by the bus is maintained within minimum changes even in the presence of transmission frames on the bus, as in the abovementioned Konnex specification. The voltage value does not have a fixed value but it is comprised within a range, because of the allowed bus voltage operating range.

Some circuits connected downstream of the $V_{ASB}$ control circuit, in particular the microcontroller for control of the whole domotic device, require a further voltage stabilizer at a much lower value, which can be realized both with switching and linear devices present on the market.

Figure 6:
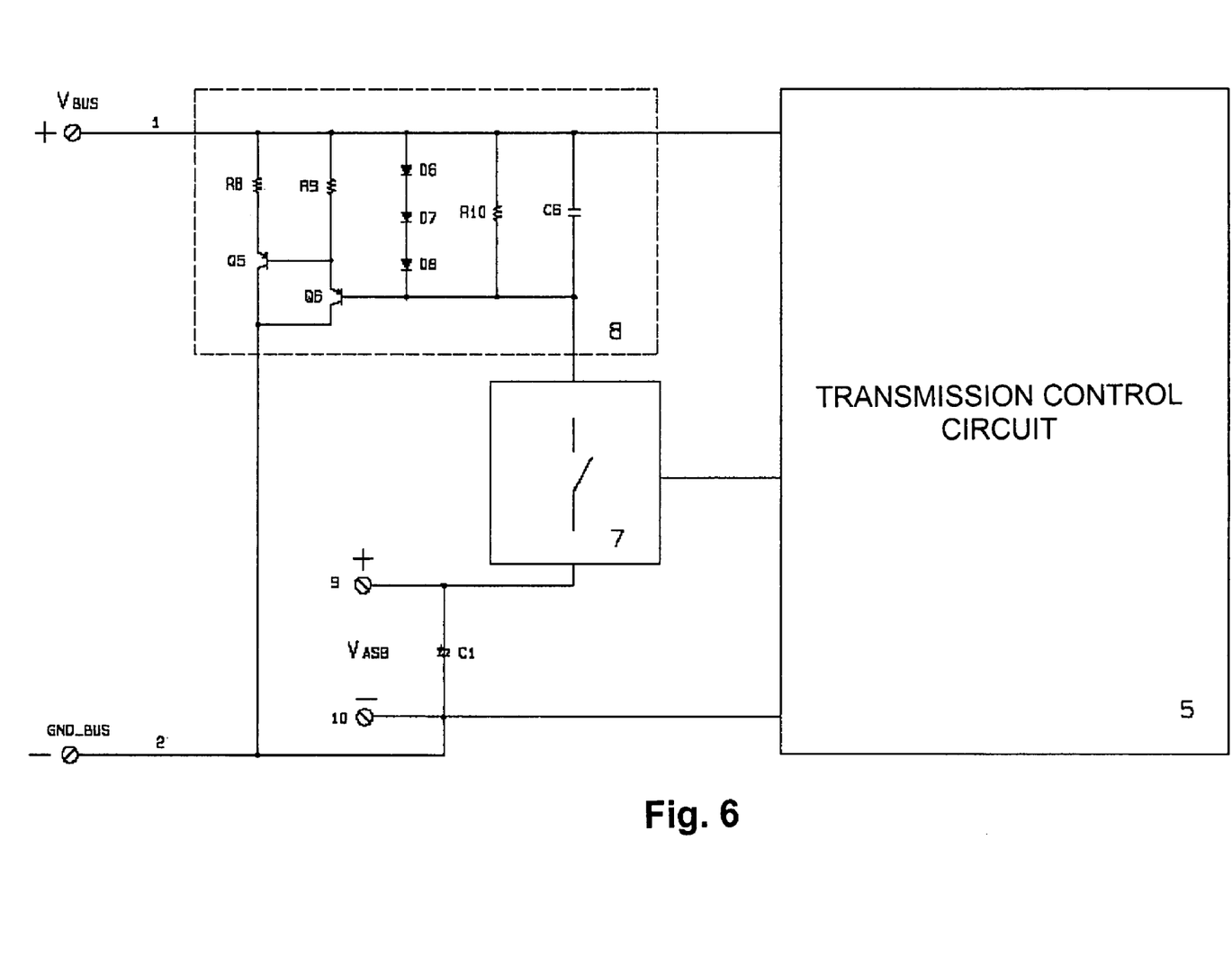
FIG. 6 is a circuit diagram illustrating in detail an embodiment of the current limiting circuit of the first module of FIG. 3.

In FIG. 6, by way of example, a possible embodiment of the current limiting circuit 8 of FIG. 3 is illustrated. The current limiting circuit 8 comprises a transistor Q5 having the collector connected to the input pin 2 and the emitter connected, by means of a resistor R8, to the input pin 1.

A transistor Q6 whose emitter is connected, by means of a resistor R9, to the pin 1 is connected between the base and the collector of Q5. The base of Q6 is connected to the switch 7.

Between the base of Q6 and the pin 1 are disposed three diodes in series D6, D7, D8 and a resistor R10 in parallel with a capacitor C6.

The transistor Q5 is a power device able to absorb the current of the bus when frames are being transmitted by the device. The transistor Q5 is controlled by the transistor Q6 disposed in a Darlington configuration.

The resistor R9 ensures that, in the absence of commands by the switch 7 (switch 7 open), the transistor Q5 is switched off. The resistor R10 on the other hand ensures that the transistor Q6 is switched off.

The diodes in series D6, D7 e D8 constitute a voltage limiter and prevent the voltage on R8 from exceeding about 0.7 V. It follows that also the current on R8 (and thus the current absorbed by the transistor Q5 during the transmission) are limited.

The capacitor C6 slows the turn-on and turn-off edges of Q5 so as to come within the Konnex specifications and to reduce any rebound phenomena due to the length of the bus line.

The current limiting circuit 8 is controlled by the electronic switch 7. At the voltage drop for the bit "0" the base of the transistor Q6 is brought to a value near to the $V_{ASB}$ voltage present on C1.

The transistor Q6 in turn controls Q5 and thus the bus voltage $V_{BUS}$ between the pins 1 and 2 drops with a front given by the charge C6. The value of $V_{BUS}$ settles at a voltage value greater than $V_{ASB}$, as a result of the various offsets given by the voltages of the bases of the transistors Q5, Q6, by the voltage on the resistor R8 and by the voltage present at the terminals of the electronic switch 7.

The current on Q5 furthermore is also limited by the circuit described above. As a result, if the transmission current exceeds the set limit, the transistor Q5 reduces the amplitude of the voltage drop. On opening of the switch 7 the transistors Q5 and Q6 are turned off with a front slowed by discharging of the capacitor C6.

Figure 7:
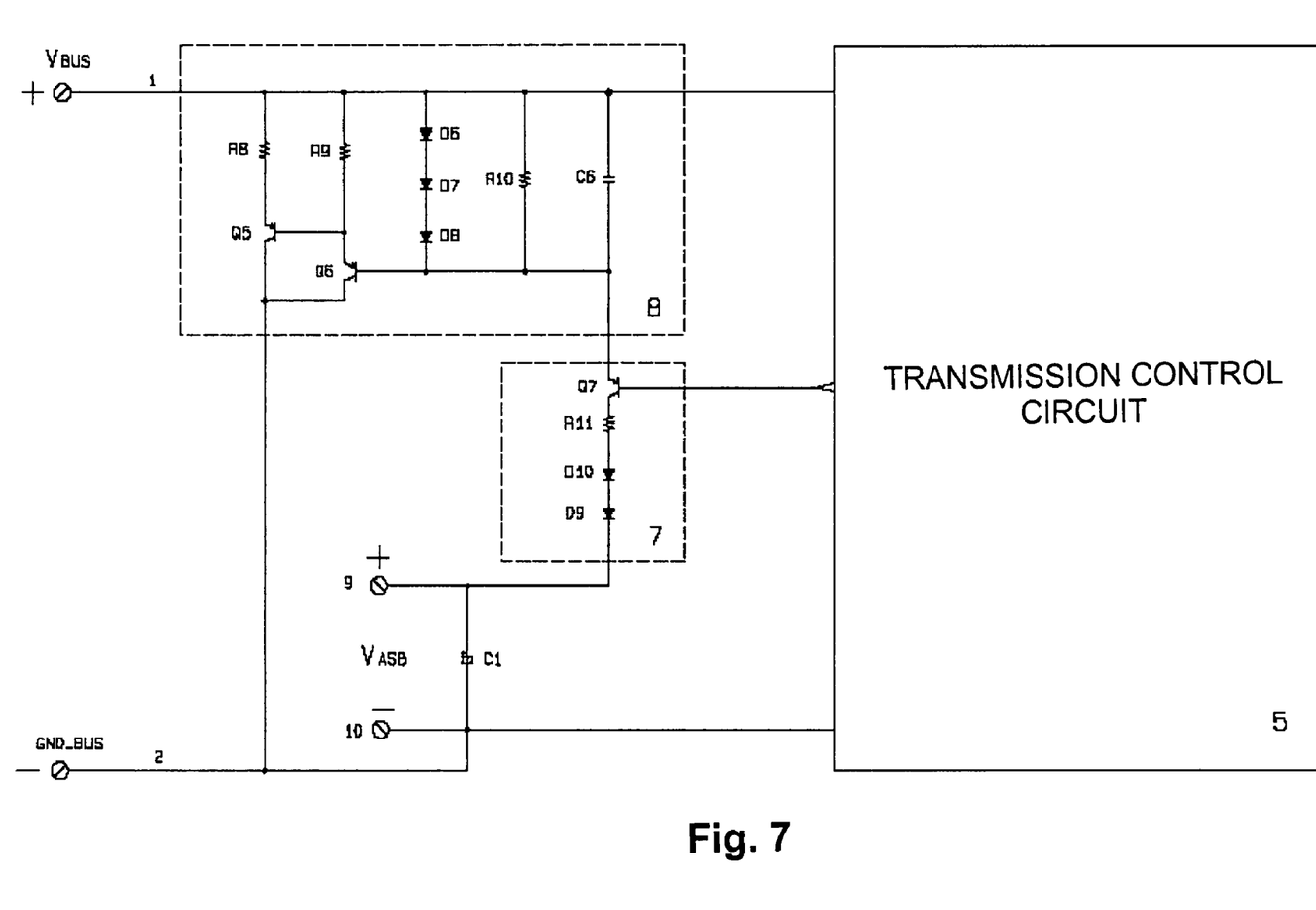
FIG. 7 is a circuit diagram, like FIG. 6, in which an embodiment of the control switch circuit is illustrated in detail.

FIG. 7 shows by way of example a possible embodiment of the controlled switch 7 of FIG. 6.

The electronic switch 7 is composed by the series of a PNP type transistor Q7, of a resistor R1 and of two diodes D9 and D10.

The diodes D9 and D10 perform the offset function between the amplitude of the voltage drop on the bus and the $V_{ASB}$ voltage. The resistor R11 serves to limit the maximum current on Q7. The transistor Q7 is controlled by the transmission control circuit 5.

Figure 8:
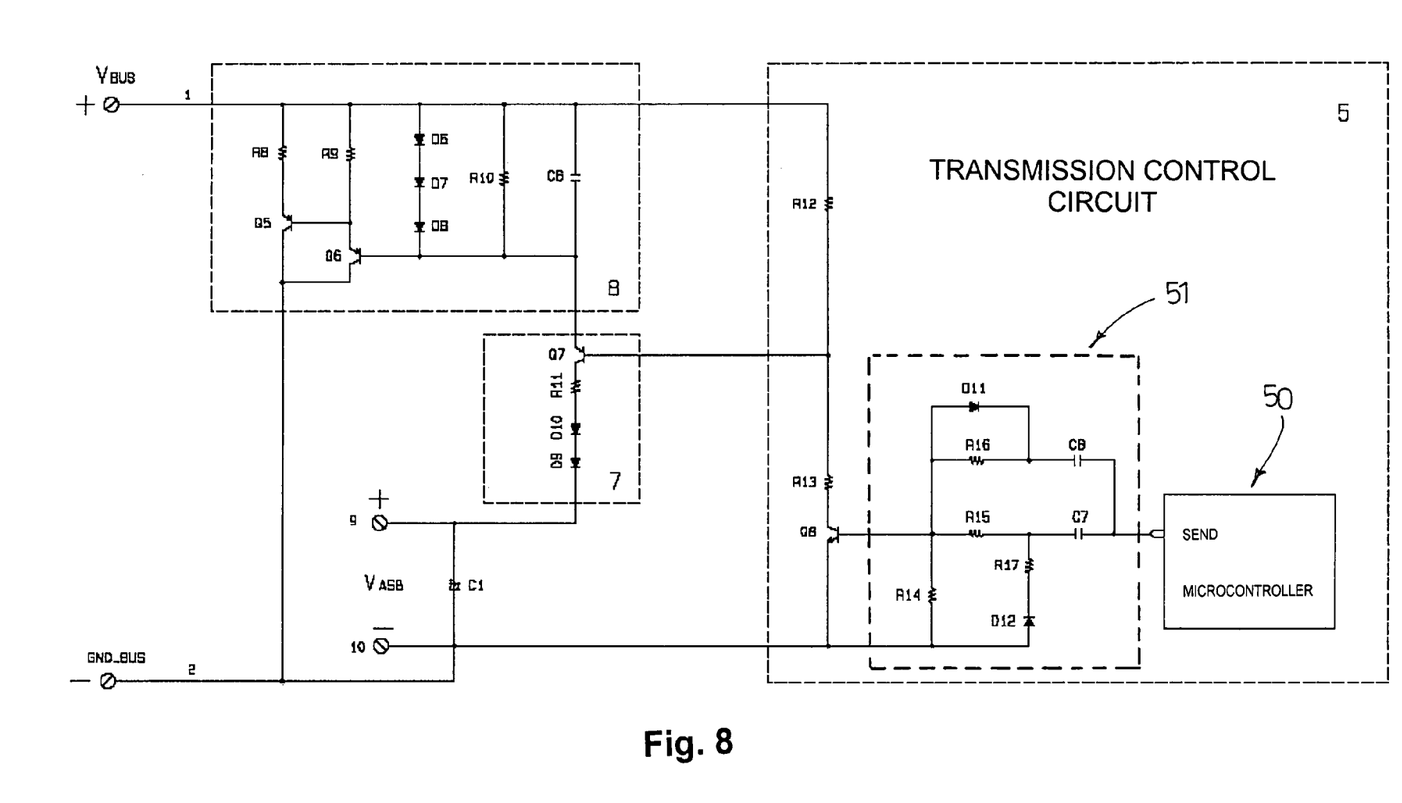
FIG. 8 is a circuit diagram, like FIG. 7, in which an embodiment of the transmission control circuit is illustrated in detail.

FIG. 8 illustrates, by way of example, a possible embodiment of the transmission control circuit 5 of FIG. 7.

The transmission control circuit 5 comprises a microcontroller 50 supplied, by means of a voltage stabilizer, with the voltage $V_{ASB}$. For simplicity's sake the electrical diagram of the microcontroller 50 is not shown, in that it can be realized with standard commercial components.

The microcontroller 50 generates a SEND signal that it emits as output by means of one of its output pins. The SEND signal, by means of an adequate coupling circuit 51, controls switching on and switching off of a transistor Q8 which in turn controls the switch 7, by means of two resistors R13 and R12 connected in series to its collector. The base of the transistor Q7 of the switch 7 is connected between the resistors R13 and R12. The coupling circuit 51 between the microcontroller 50 and the transistor Q8 has the dual function of obtaining a suitable switching on and switching off speed of Q8 and of limiting the maximum duration of the switching on time of Q8.

There follows a description of the coupling circuit 51. The SEND pin of the microcontroller is connected to two capacitors C7 and C8 connected in series to respective resistors R15 and R16 connected to the base of Q8. A diode D11 is connected in parallel to the resistor R16. A resistor R17 has one terminal between the capacitor C7 and the resistor R15 and the other terminal connected to a diode D12 in turn connected to the emitter of Q8. A resistor R14 is disposed between the base and the emitter of Q8.

When the SEND signal switches from low to high, the transistor Q8 is switched on by means of the current through C7 and R14. The capacitor C8 is charged through R16.

The charge constant of C7 is calculated so as to ensure that for the entire duration of the high SEND signal (typically 35 μs) the transistor Q8 remains on.

However, in the eventuality of a SEND signal remaining blocked high following a malfunction, the capacitor C7, once it is charged, cuts off the base current of Q8 which is therefore switched off. This ensures a protection on the maximum duration of the current through the power transistor Q5 of the current limiter 8 which could otherwise break.

When the SEND signal switches from high to low, the transistor Q8 is switched off quickly, thanks to the capacitor C8, which empties the base charges, and to the resistor R14. At the same time C7 is discharged thanks to D12 and R17.

In addition to the first module 100, the modem according to the invention can comprise a second module 200. like that shown in FIG. 4.

The second module 200 of the modem comprises two input pins 11 and 12 destined to be connected to the bus and two output pins 16 and 17 destined to be connected to the circuit of devices connected to the bus, such as, for example, bistable relays.

Between the input pins 11 and 12 there is disposed a $V_{M\_BUS}$ control circuit able to control the $V_{M\_BUS}$ voltage at the terminals of the output pins 16 and 17. The $V_{M\_BUS}$ control circuit is connected, by means of a connection 14, to a capacitor C2 disposed between the output pins 16 and 17. Thus the $V_{M\_BUS}$ control circuit maintains the capacitor C2 charged to control the voltage at the terminals of the pins 16 and 17.

The object of the $V_{M\_BUS}$ control circuit is to obtain a stabilized voltage equal to the mean voltage value of the bus $V_{BUS}$, typically the direct voltage value, but without compromising or significantly interfering with the transmitted frames.

To this purpose the maximum absorbed current must be limited to about 1 mA, by means of a constant current circuit. Furthermore this makes it possible to come within the limits imposed by the Konnex test specifications for pulse-impedance.

A typical application of the second module 200 are bistable relays which require particularly high switching current pulses, but for very short times. The capacitor C2, suitably sized, stores all the energy necessary to control the relays. The necessary recharge is obtained very slowly by means of a current limited circuit.

In general the circuit makes it possible to provide a power supply with a mean power consumption of about 1 mA. Any absorption peaks are guaranteed by the capacitor C2, suitably sized.

Figure 9:
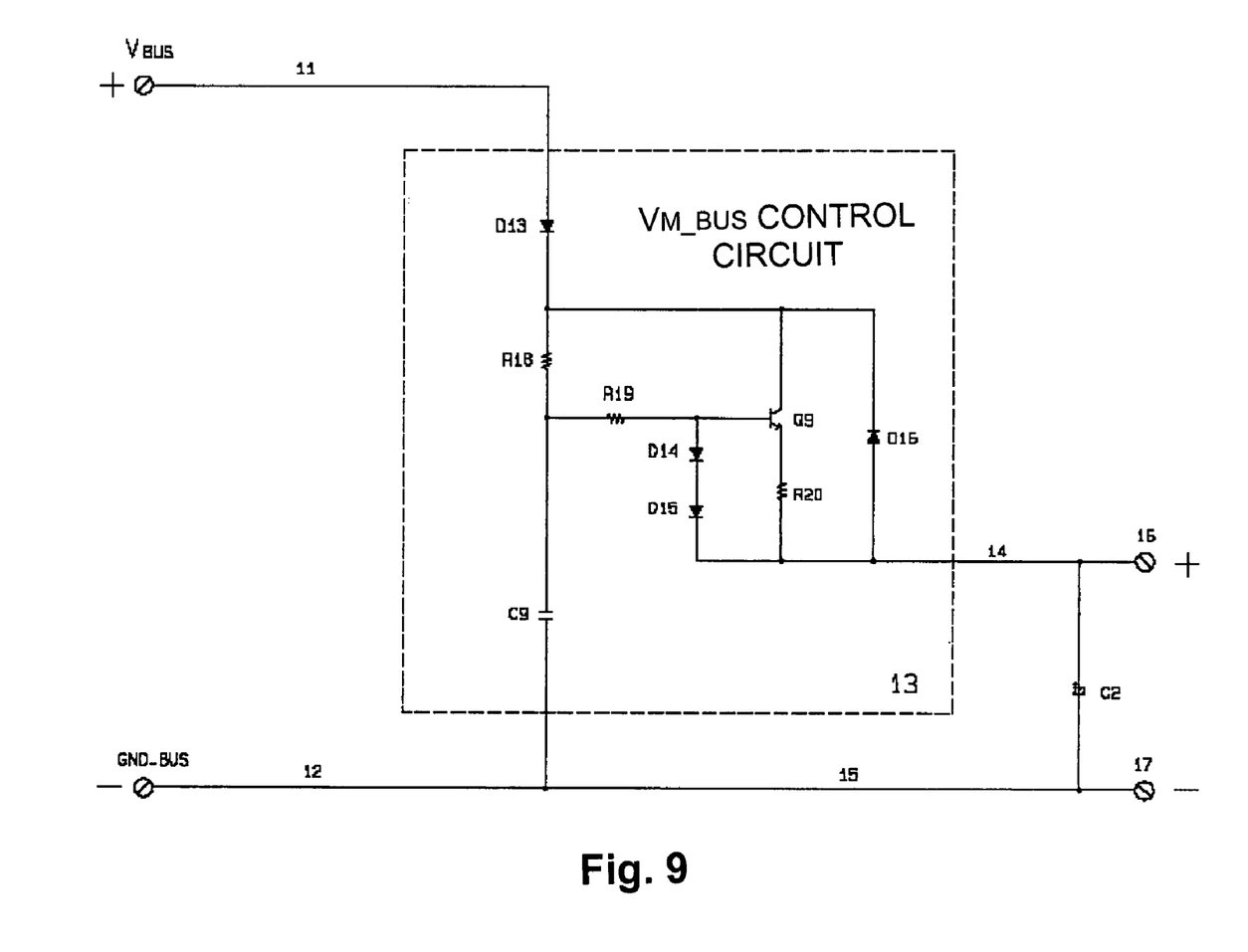
FIG. 9 is a circuit diagram illustrating in detail an embodiment of the control circuit $V_{M\_BUS}$ of the second module of FIG. 4.

FIG. 9 illustrates by way of example a possible embodiment of the $V_{M\_BUS}$ control circuit of FIG. 4.

A diode D13, a resistor R18 and a capacitor C9 are disposed in series between the input pins 11 and 12. A resistor R19 has one terminal connected between R18 and C9 and the other terminal connected to the base of a transistor Q9.

The collector of Q9 is connected between D13 and R18 and the emitter is connected, by means of a resistor R20, to a connection 14 connected to the output pin 16. A diode D16 is connected between the emitter and the collector of Q9.

The diode D13 ensures that the current is one-way from the bus to the accumulation capacitor C2. The mean voltage value present on the bus is obtained by means of R18 and C9. This voltage is used to control a current limited transistor Q9.

The two diodes D14 and D15 provide a voltage limit which limits the voltage on R20 to about 0.7V. This also determines a limit on the current on R20 and thus also on Q9, that is, on the current taken by the bus. The diode D16 serves to avoid excessive inverse voltages being generated on the transistor Q9 in the absence of voltage on the bus and with the capacitor C2 still charged.

Numerous variations and modifications of detail within the reach of a person skilled in the art can be made to the present embodiments of the invention without thereby departing from the scope of the invention, as set forth in the appended claims.

The invention claimed is:

1. A bus modem for building and industrial electrical systems comprising a module which comprises a pair of input pins destined to be connected to the bus and a pair of output pins destined to be connected to the electrical circuit of a device to be connected to the bus, characterized in that said module further comprises:
    a voltage control circuit able to take the voltage from said bus and to control the voltage on a capacitor disposed at the terminals of said output pins, and
    a transmission control circuit able to control an electronic switch, which controls a current limiting circuit able to limit the current on the bus during transmission of signals from the bus to the devices connected to the bus and vice versa.

2. A modem according to claim 1, characterized in that said voltage control circuit comprises a capacitor that is charged and stabilized by means of a charging circuit connected to the terminals of the input pins in order to control the voltage on the capacitor by means of a voltage stabilizing circuit.

3. A modem according to claim 2, characterized in that said charging circuit of the capacitor comprises a Zener diode connected to a resistive divider.

4. A modem according to claim 2, characterized in that said voltage stabilizing circuit comprises at least one stabilizer transistor whose emitter is connected, by means of at least one resistor and of at least one diode, to said capacitor on which the voltage must be stabilized.

5. A modem according to claim 4, characterized in that said voltage stabilizing circuit comprises a current amplifying transistor whose emitter is connected to the base of at least one stabilizer transistor.

6. A modem according to claim 2, characterized in that said voltage control circuit comprises a power consumption reducing circuit able to reduce the power consumption of the control circuit.

7. A modem according to claim 6, characterized in that said power consumption reducing circuit comprises a capacitor connected, by means of a resistive divider, to a transistor whose collector is connected by means of a resistor to a capacitor connected to said voltage stabilized capacitor.

8. A modem according to claim 1, characterized in that said current limiting circuit comprises a power transistor with emitter and collector connected to said pair of input pins controlled by a polarizing circuit, able to limit the voltage between base and emitter of said power transistor.

9. A modem according to claim 8, characterized in that said polarization circuit of said power transistor comprises a transistor in Darlington configuration and at least one diode, in parallel with a resistor and with a capacitor, positioned between the base of said transistor and the input pin.

10. A modem according to claim 1, characterized in that said electronic switch comprises a transistor wherein the base of said transistor is connected to said transmission control circuit (5) and the emitter and the collector of said transistor are connected to said current limiting circuit (8) and to an output pin of said module, respectively.

11. A modem according to claim 10, characterized in that between the collector of said transistor of the switch and said output pin of the module there is interposed a resistor in series with at least one diode.

12. A modem according to claim 1, characterized in that said transmission control circuit comprises a microcontroller able to send a control signal to said switch.

13. A modem according to claim 12, characterized in that said transmission control circuit comprises a transistor whose collector is connected to said switch and a coupling circuit which couples the base of said transistor to said microcontroller.

14. A modem according to claim 1, characterized in that it comprises a second module comprising:
  a pair of input pins destined to be connected to the bus,
  a pair of output pins destined to be connected to the electrical circuit of a device to be connected to the bus, and
  a voltage control circuit able to take the voltage from said bus and to control the voltage on a capacitor disposed at the terminals of said output pins.

15. A modem according to claim 14, characterized in that said voltage control circuit comprises a transistor able to take the current from the bus and to send it to said output pins of the second module.

16. A modem according to claim 15, characterized in that said voltage control circuit comprises a diode, a resistor and a capacitor disposed in series at the terminals of the input pins and wherein between the base and the emitter of said transistor there are disposed at least a diode and a resistor and between the emitter and the collector of said transistor there is a diode.

* * * * *